(12) United States Patent
Schmid et al.

(10) Patent No.: US 9,352,504 B2
(45) Date of Patent: May 31, 2016

(54) METHOD FOR MANUFACTURING OF A TUBULAR OBJECT FOR INSERTION INTO A BODY PASSAGEWAY

(75) Inventors: Andrea Schmid, Mölnlycke (SE); Mats Andersson, Hisings Backa (SE)

(73) Assignee: DENTSPLY International Inc., York, PA (US)

( * ) Notice: Subject to any disclaimer, the term of this patent is extended or adjusted under 35 U.S.C. 154(b) by 216 days.

(21) Appl. No.: 13/461,828

(22) Filed: May 2, 2012

(65) Prior Publication Data

US 2013/0116662 A1 May 9, 2013

Related U.S. Application Data

(60) Provisional application No. 61/481,494, filed on May 2, 2011.

(30) Foreign Application Priority Data

May 2, 2011 (EP) ..................................... 11164474

(51) Int. Cl.
| | | |
|---|---|---|
| B29C 47/00 | (2006.01) | |
| A61F 5/453 | (2006.01) | |
| B29C 57/04 | (2006.01) | |
| B29D 23/00 | (2006.01) | |

(Continued)

(52) U.S. Cl.
CPC ............. *B29C 47/0066* (2013.01); *A61F 5/453* (2013.01); *A61M 25/0009* (2013.01); *A61M 25/0017* (2013.01); *B29C 47/0023* (2013.01); *B29C 47/0038* (2013.01); *B29C 57/04* (2013.01); *B29D 23/001* (2013.01);

(Continued)

(58) Field of Classification Search
CPC ....................................................... B29C 57/04
USPC ............................... 425/297, 403, 133.1, 393
See application file for complete search history.

(56) References Cited

U.S. PATENT DOCUMENTS 3,677,684 A * 7/1972 Platz ............................ 425/393
3,708,253 A * 1/1973 Lemelson ..................... 425/155

(Continued)

FOREIGN PATENT DOCUMENTS

| EP | 0950425 A2 | 3/1999 |
| EP | 0917108 B1 | 9/2002 |
| GB | 744327 | 2/1956 |
| GB | 2284764 A | 6/1995 |

OTHER PUBLICATIONS

European Search Report, Application No. 11164474.6, Published Aug. 17, 2011.

*Primary Examiner* — Yogendra Gupta
*Assistant Examiner* — Kimberly A Stewart
(74) *Attorney, Agent, or Firm* — Leana Levin; Douglas J. Hura; David A. Zdurne

(57) ABSTRACT

Disclosed are a method and an apparatus for manufacturing a medical tubular object, such as a catheter, for insertion into a body passageway. The method comprises the steps of extruding a tube by pushing tube material though an extrusion nozzle and cutting the extruded tube at a predetermined length. Further, an initial part of the extruded tube is advanced onto a tapered mandrel arranged adjacent the extrusion nozzle such that a flared end is formed, and after a predetermined length of the extruded tube has been advanced onto the tapered mandrel, the tapered mandrel is moved away from the extrusion nozzle to prevent that the rest of the extruded tube is expanded by the tapered mandrel.

12 Claims, 5 Drawing Sheets

(51) Int. Cl.
*A61M 25/00* (2006.01)
*B29C 47/20* (2006.01)
*B29C 47/34* (2006.01)
*B29L 31/00* (2006.01)
*B29C 47/08* (2006.01)

(52) U.S. Cl.
CPC ............ *B29C47/0876* (2013.01); *B29C 47/20* (2013.01); *B29C 47/34* (2013.01); *B29L 2031/7542* (2013.01)

(56) References Cited

U.S. PATENT DOCUMENTS

| | | | | |
|---|---|---|---|---|
| 4,157,503 | A | * | 6/1979 | Brunner ..................... 324/231 |
| 4,234,301 | A | * | 11/1980 | Hayes et al. ................. 425/392 |
| 4,250,072 | A | | 2/1981 | Flynn |
| 5,948,332 | A | * | 9/1999 | Prenger ....................... 264/40.5 |
| 2007/0006964 | A1 | * | 1/2007 | Lee ............................... 156/219 |
| 2008/0193583 | A1 | | 8/2008 | Kikusawa |

* cited by examiner

METHOD FOR MANUFACTURING OF A TUBULAR OBJECT FOR INSERTION INTO A BODY PASSAGEWAY

RELATED DOCUMENTS

This application claims the benefit of priority U.S. provisional application Ser. No. 61/481,494, filed May 2, 2011 and European application Ser. No. 11164474.6, filed May 2, 2011, which are herein incorporated by reference for all purposes.

FIELD OF THE INVENTION

The present invention relates to an apparatus and a method for manufacturing a tubular object, such as a tube or a catheter, for insertion into a body passageway.

BACKGROUND OF THE INVENTION

Many types of medical devices having a tubular object for insertion into a body passageway are known, such as urinary catheters, stents, etc. These tubular objects conventionally comprise an insertable end provided with one or more draining openings such that fluid can enter the tube, and a non-insertable end provided with an outlet being in fluid connection with the draining openings via the tube. The non-insertable end of the tubular object may advantageously be flared. A flared end can prevent that the tubular object is pushed so far into the body passageway that the non-insertable end of the tubular object disappears into the body passageway. A flared end also makes it easier for an operator to get hold of the tubular object when it should be removed the body passageway. The flared end may also serve as a connector for connecting the tubular object to a receptacle.

Various techniques for producing tubular objects with a flared end are known, some of which involves extrusion. For example, GB 744 327 discloses an extrusion process for forming an endless tube. The extruded tube is cut into suitable lengths, and subsequently, a tip portion and a flared end portion are formed at the respective ends. Formation of the flared end is made by pushing the extruded end over a conical or frusto-conical mandrel during simultaneous heating, and the thus formed part is thereafter immediately cooled in order to obtain a permanent deformation. However, this known method is relatively cumbersome and costly, and does not lend itself for fully automated manufacturing.

However, although this process allows manufacturing of catheter tubes with a flared end, there is a need for a more efficient production process.

SUMMARY OF THE INVENTION

It is therefore an object of the present invention to provide a more efficient process for manufacturing of the tubular objects with a flared end.

This object is achieved with a method and apparatus according to the appended claims.

According to an aspect of the invention there is provided a method for manufacturing a medical tubular object, such as a catheter, for insertion into a body passageway, comprising the steps of: extruding a tube by pushing tube material though an extrusion nozzle; and cutting the extruded tube at a predetermined length, wherein the method comprises the further steps of: advancing an initial part of the extruded tube onto a tapered mandrel arranged adjacent the extrusion nozzle such that a flared, or funnel-shaped, end is formed; and after a predetermined length of the extruded tube has been advanced onto the tapered mandrel, moving the tapered mandrel away from the extrusion nozzle to prevent that the rest of the extruded tube is expanded by the tapered mandrel.

The term "tubular object" as used herein refers to an object at least part of which forms a tube. The term "tube" here refers to an elongated shaft with a lumen therein. The tube may typically be an elongate hollow cylinder, but may also be a hollow shaft of other cross-sectional shapes.

The term "tapered mandrel" indicates a mandrel with a cross-sectional area that increases in the direction of extrusion. For example, the tapered mandrel may have a conical or frusto-conical shape. However, the tapered mandrel may also take other shapes that allow formation of a flared or funnel-shaped end of the tube.

Even though the flared end formed by the mandrel generally has a circular cross-section, it is to be acknowledged by the skilled addressee that non-circular cross-sections, such as oval or elliptical cross-sections are also feasible, and may be formed in the same way by providing a corresponding shape of the mandrel. Further, the flared end may similarly be formed with varying thickness around its circumference and/or along its length.

The present invention is based on the realization that by using a moveable tapered mandrel, an initial part of the extruded tube can be expanded into a flared end immediately after the tube leaves the extrusion nozzle. Then the tapered mandrel can be moved away such that it does not interfere with extrusion of the rest of the tube. As the formation of the flared end of the tube is integrated in the extrusion process, a more efficient production process can be achieved compared to prior art methods.

Further, as the flared end is formed immediately after the extruded tube has left the extrusion nozzle, the tube material is still pliable and a flared end can be formed without any preparatory work, such as heating, that may otherwise be required. However, for certain materials, for example some thermoplastic polymers, such as polyethylene, additional heating may be used. Such additional heating may e.g. be provided by internal heating of the mandrel, or by external application of the heating, e.g. by directing a hot air stream towards the mandrel. However, many other ways of accomplishing local heating are also feasible.

The immediate advancement of the initial part of the extruded tube onto the tapered mandrel are also highly advantageous for many other reasons. For example, this leads to a very fast and efficient manufacturing process, since exact positioning of the tube on the mandrel becomes very simple, whereby no time and cost consuming post positioning is to get the tube into position to form the flared end. The risk for cassation is also alleviated. Further, since the connector is formed as an integrated part of the manufacturing of the tube, no separate glueing of connector to a shaft is necessary, and there is also a reduced risk for breakage between the shaft and the connector. Still further, since the material used in the shaft and the material used in the connector, share the same manufacturing history, the properties of these materials are more controllable.

This integrated procedure also leads to less cumbersome and tedious handling of the material, compared to e.g. extrusion of a tube and subsequent forming of a flared end after extrusion. This also leads to an energy effective production. Further, the integrated production also leads to less harm to the material, since there is no need for repeated subsequent heating and cooling of the material. At the end, this also leads to an increased quality of the end product.

A flared end can prevent that the tubular object is pushed so far into the body passageway that the non-insertable end of the tubular object disappears into the body passageway. A flared end also makes it easier for an operator to get hold of the tubular object when the tubular object should be removed from the body passageway. The flared end may also serve as a connector for connecting the tubular object to a receptacle.

The tapered mandrel may be moved, or displaced, in a direction of the extrusion. This allows extrusion of a substantially straight tube while the tapered mandrel remains within the flared end. It also allows the tapered mandrel to be removed from the flared end of the tubular object.

The tapered mandrel may be moved at a speed that substantially corresponds to a speed at which the extruded tube is produced. An advantage is that the tapered mandrel can remain within and support the flared end throughout the extrusion process.

The method may comprise securing the flared end of the extruded tube at the tapered mandrel. This can be achieved by means of a clamping arrangement arranged to press the flared end of the tube against the mandrel. Thus, even if the speed at which the tube is extruded is occasionally reduced, the tapered mandrel remains within the flared end. The clamping arrangement also has the additional purpose and advantage of assisting in forming the flared end to the desired shape over the mandrel. Thus, the clamping arrangement preferably serves the dual functions of both securing the flared end to the mandrel and shaping the flared end into the desired shape.

The tube material may comprise at least one of monosaccharide, disaccharide, oligosaccharide and polysaccharide. For example, the tube material may primarily comprise water, at least one of sugar and starch and gelatin. Tube materials comprising these ingredients may form degradable materials that may be totally dissolved if maintained in water, and have also been found to be particularly suitable for extrusion. However, the above manufacturing method can also be used for polymers, such as polyethylene, polypropylene or polyvinyl chloride, or any other material suitable for extrusion.

The tube material may be heated before and/or during extrusion, but may also be performed at room temperature. For example, provision of heat may be advantageous for certain thermoplastic polymers, such as polyethylene. However, for the many materials where the formability of the material at room temperature is sufficient to form a tube and a flared end, additional heat is not required. To maintain the form, cooling or drying might be used.

Subsequently, after the extruded tube has been cut, an end of the tube opposite the flared end may be formed into a rounded tip portion, said forming preferably involving melting.

Preferably, at least one, and preferably two or more, of a punching means, a cutting means and a rounded tip forming means is arranged in the vicinity of the extrusion nozzle. These means are preferably moveable in a direction towards and away from the extruded tube. Further, the extrusion nozzle further comprises a centrally protruding pin, wherein the extrusion nozzle is arranged to extrude the tube over said centrally protruding pin. The centrally protruding pin may serve as an abutment or positive stop for the cutting and/or the punching actions, and may also serve the purpose of maintaining the shape of the extruded tube during punching and/or cutting.

Moreover, an opening may be formed in the tube wall, said forming preferably comprising at least one of punching and blank cutting. The opening may serve as a drainage opening that allows fluid to enter a lumen of the tube.

The method is particularly useful for manufacturing of catheters, and most preferably urinary catheters.

According to another aspect of the present invention there is provided an apparatus for manufacturing a medical tubular object, such as a catheter, for insertion into a body passageway, comprising: an extrusion nozzle adapted to extrude a tube; an extruder arranged to push tube material through the extrusion nozzle; a cutting means for cutting the extruded tube at a predetermined length; and a tapered mandrel arranged adjacent the extrusion nozzle such that an initial part of the extruded tube is advanced onto the tapered mandrel whereby a flared end is formed, wherein the tapered mandrel is moveable such that the tapered mandrel can be moved away from the extrusion nozzle after a predetermined length of the extruded tube has been advanced onto the mandrel, to prevent that the rest of the extruded tube is expanded by the tapered mandrel.

Hereby, similar advantages as discussed above in relation to the previous aspect of the invention are achieved.

The above described method and apparatus may be used to produce a tube that constitutes, or is part of, a medical device, such as a catheter, stent, etc. In particular, the above described method and apparatus is suitable in a process for producing urinary catheters.

These and other aspects of the invention will be apparent from and elucidated with reference to the embodiment described hereinafter.

BRIEF DESCRIPTION OF THE DRAWINGS

These and other aspects of the present invention will now be described in more detail, with reference to the appended drawings showing embodiment(s) of the invention.

DESCRIPTION OF PREFERRED EMBODIMENTS

In the following detailed description, preferred embodiments of the present invention will be described. However, it is to be understood that features of the different embodiments are exchangeable between the embodiments and may be combined in different ways, unless anything else is specifically indicated. Even though in the following description, numerous specific details are set forth to provide a more thorough understanding of the present invention, it will be apparent to one skilled in the art that the present invention may be practiced without these specific details. In other instances, well known constructions or functions are not described in detail, so as not to obscure the present invention The invention will in the following be discussed in relation to a urinary catheter. However, it is to be noted that the same technical teaching may also be used for producing of other types of medical devices insertable into a body passageway, such as other types of catheters, stents, etc.

Figures 1A, 1B:
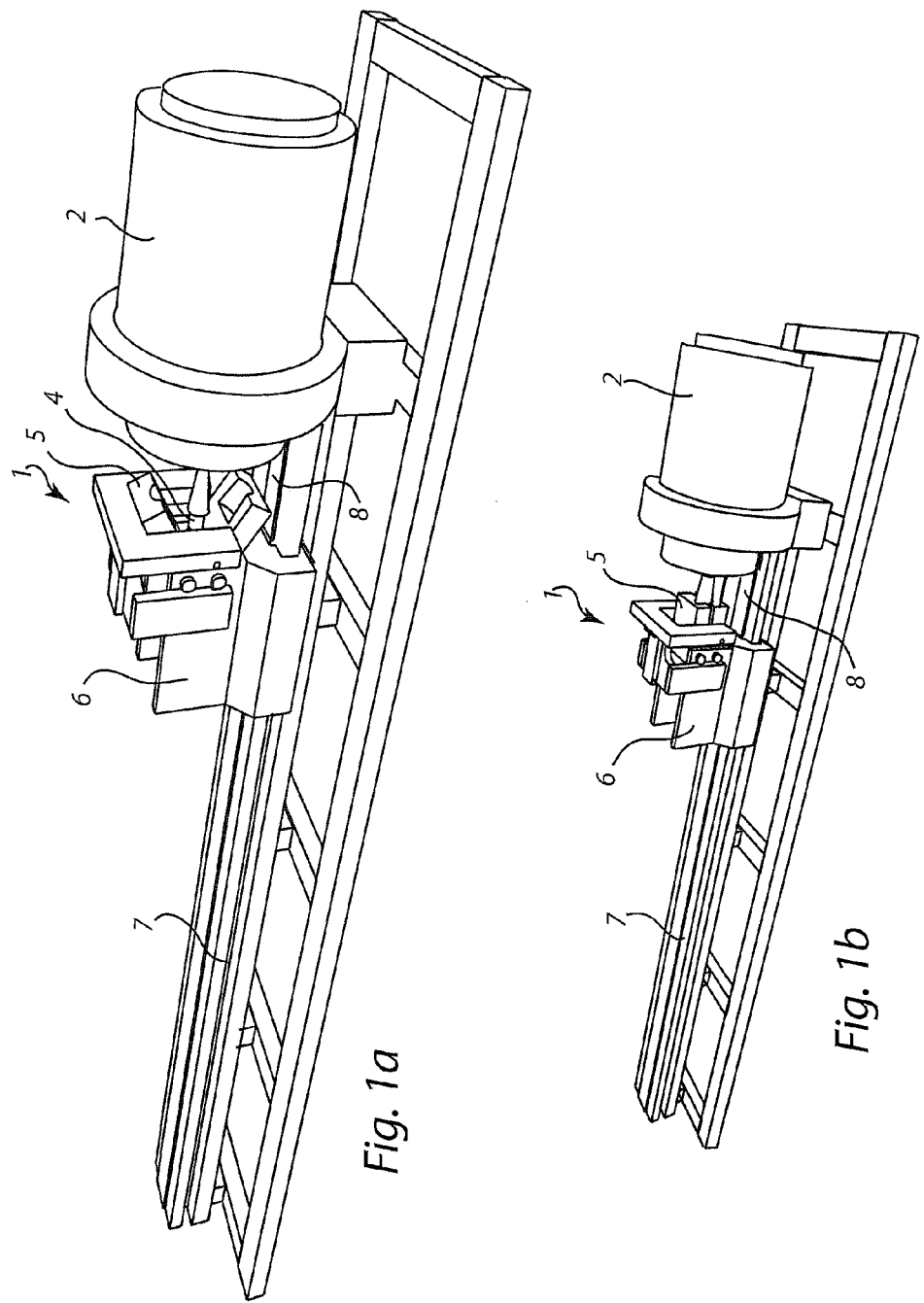
FIGS. 1a and 1b are perspective views schematically illustrating an apparatus according to an embodiment of the invention, with the clamping arrangement in an open and closed position, respectively.

FIGS. 1a and 1b schematically illustrate an apparatus according to an embodiment of the invention for manufacturing a catheter tube for insertion into a urethra. The apparatus 1 comprises an extruder 2, which will normally include a mixing screw (not shown) leading to an extrusion nozzle 3, such as a die. The apparatus can also include a cutting means (not shown) for cutting the extruded tube at a predetermined length. Extruders as such are well-known in the art, and no detailed explanation will be provided on the mechanics thereof. An example of an extruder is described in US2008/0193583, which is hereby incorporated by reference.

The apparatus 1 further includes a tapered mandrel 4 arranged adjacent the extrusion nozzle 3, and being movable in a direction of the extrusion. The tapered mandrel is arranged such that its cross-sectional area increases in the direction of extrusion. The tapered mandrel preferably has a conical or frusto-conical shape. The mandrel 4 is preferably arranged on a holding structure 6, which is movable along a guide rail 7 in a direction towards and away from the extruder 2.

The apparatus preferably includes an openable clamping arrangement 5 that can be closed around the tapered mandrel. Here, the clamping arrangement includes two clamping elements that are arranged on opposite sides of the tapered mandrel. The clamping elements are configured such that, when the clamping elements are closed around the tapered mandrel, the portion of an extruded tube that has been advanced onto the tapered mandrel is pressed against the tapered mandrel such that funnel-shaped connector end is formed. Further, a sensor (not shown) may be used to determine a suitable positioning of the extruded tube on the mandrel before closing of the clamping arrangement. As the extruded tube advances onto the tapered madrel the sensor hereby activates the closing of the clamping elements e.g. at a position where the material covers the tapered mandrel. When the clamping elements are closed the funnel shaped material on the tappered mandrel surrounded by the clamping elements is moved away from the extrusion nozzel and in the same direction as the extrusion direction, at a speed suitable for forming a tube.

In the illustrated example, the clamping arrangement comprises two parts which are moveable in relation to each other. However, the clamping arrangement may instead comprise 3, 4, or more parts, depending on the desired shape and design of the funnel shaped end.

The surface finish of the funnel shaped end might be smooth, or vary in roughness, depending on the design of the outside of the connector. The degree of smoothness/roughness may be controlled by arranging a corresponding smoothness/roughness on the inner side of the clamping arrangement. Further, the inner side of the clamping arrangement may be used to form embossment, corrugation and the like on the outer surface of the funnel shaped end. For example, the inner side of the clamping arrangement may be used to emboss or form a trade name on the funnel shaped end of the tubular object.

A holding means 8, such as a holding plate, may be arranged beneath the extruded material, to maintain the extruded tube in a relatively straight, and preferably essentially horizontal position. The holding plate may e.g. be connected to a rearward part of the clamping arrangement, and be arranged to be withdrawn along with the mandrel as it is moved away from the extruder.

FIG. 1a illustrate the apparatus with the clamping arrangement 5 in an opened position, whereas FIG. 1b illustrate the clamping arrangement 5 in a closed position.

Figure 2A:
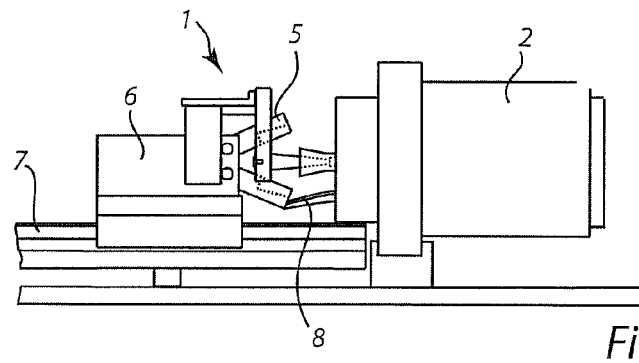
FIG. 2a-d are side views schematically illustrating a working sequence of the apparatus of FIG. 1.
Figure 2B:
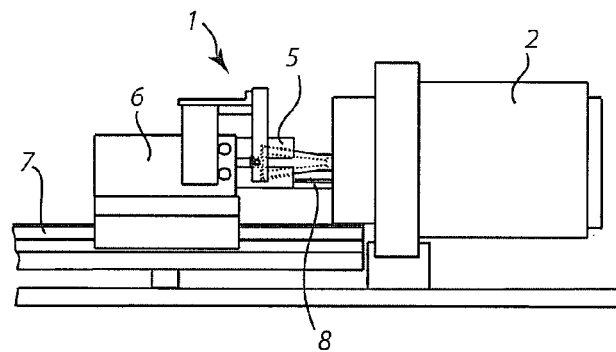
Figure 2C:
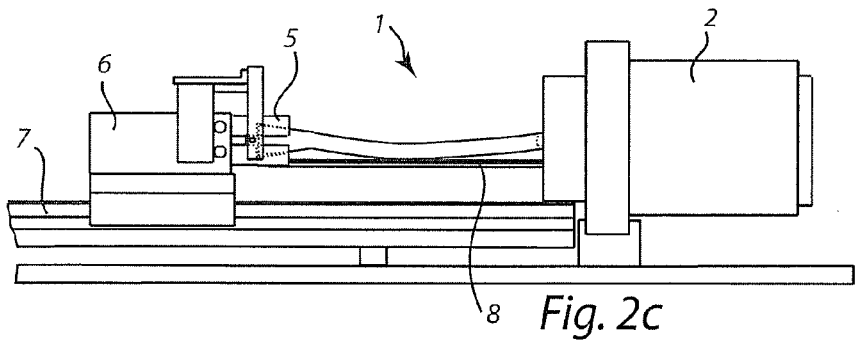
Figure 2D:
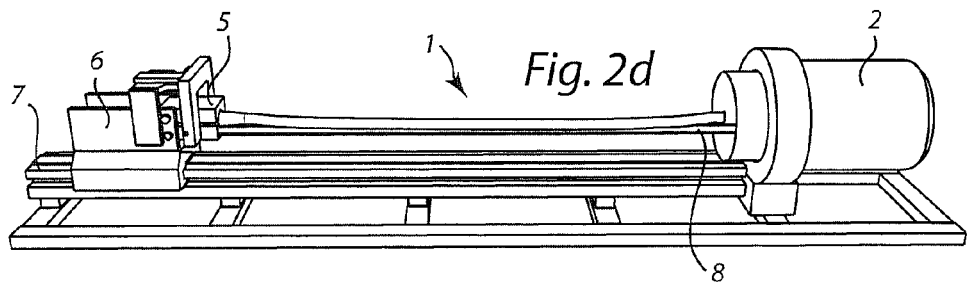
Figure 3:
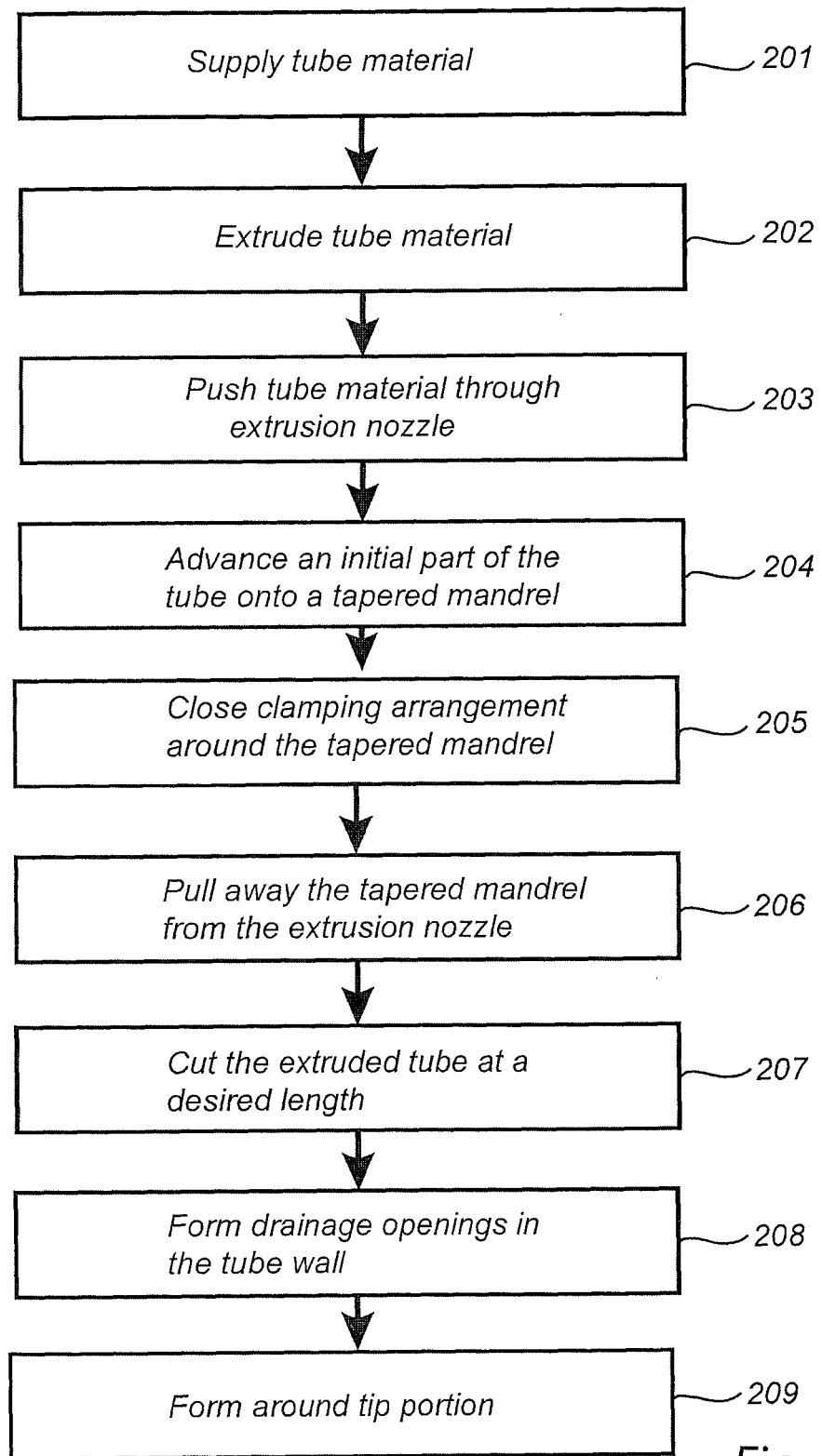
FIG. 3 is a flow chart illustrating process steps for manufacturing a urinary catheter according to an embodiment of the invention.

A process for manufacturing a catheter tube using the apparatus of FIG. 1 will now be described with further reference to the flow chart in FIG. 3 and the sequential drawings FIGS. 2a-d.

To produce a catheter tube, a tube material is placed in the extruder 2, in step 201. The tube material may vary e.g. depending on the desired characteristics of the resulting catheter tube. However, the process has been found to be particularly suitable for extrusion of degradable catheter tubes, i.e. catheter tubes that can be totally dissolved if maintained in water. Degradable catheter tubes are preferably primarily made of sugar and/or starch, and preferably comprise at least one of monosaccharide, disaccharide and polysaccharide. Examples of such materials are known from the previous application with application number EP09171080 by the same applicant, which is hereby incorporated by reference.

In an exemplary embodiment, the degradable material for extrusion comprises brown syrup (50 kg), black syrup (25 kg), flour (40 kg) water (16+19 kg), liquorices (3 l), carbon black (1 liter), sodium chloride (500 ml), ammonium chloride (7 kg), water (1 liter) and anise oil (60 ml). The brown syrup, flour and water (16 kg) are mixed at room temperature until homogenous. NaCl was added and the mixture heated to 90° C. until 65-67% water content. Black syrup water (19 kg), liquorices+1 l wate, carbon black is added and mixed, and subsequently heated to 98° C. until 70-72% water content is reached. Salmiak (aq) and anise oil is added and mixed. Thereafter, the mixture rested for 12 h at room temperature, and is then ready for extrusion.

The extruder 2 is then operated, in step 202, to extrude the tube material, e.g. by initiating the turning of the screw which advances the tube material towards the extrusion nozzle. The tube material can be extruded at room temperature in a "cold press" screw extruder without temperature zones. However, it may also be possible to heat the tube material before and/or during extrusion. Preferably, the extruder is operated at room temperature, i.e. 23-25° C. However, due to the pressure and friction obtained during extrusion, the temperature within the extrusion screw will, even when operated at room temperature without additional heating, often be higher. For example, during extrusion with the above-discussed exemplary material at room temperature, wherein a pressure of 4-10 kPa was exerted, a temperature within the extrusion screw of up to ca 50° C. was obtained.

As the tube material is pushed through the extrusion nozzle 3, in step 203, an extruded tube 6 is formed. An initial part of the extruded tube is immediately advanced onto the tapered mandrel 4, in step 204, and expanded such that a flared, or funnel-shaped, end 7 is formed. This is schematically illustrated in FIG. 2a. After a predetermined length of the extruded tube has been advanced onto the tapered mandrel such that a desired length of the tube has been expanded, the clamping arrangement 5 is closed around the tapered mandrel, in step 205. This is schematically illustrated in FIG. 2b. As the clamping elements press the flared end of the tube against the tapered mandrel, the flared end is secured at the mandrel. Additionally, the clamping arrangement may be configured to form the flared into a desired shape.

In step 206, the tapered mandrel 4 is pulled away from the extrusion nozzle 3, in the direction of extrusion, and at the same speed as the extruded tube 6 is produced. This is schematically illustrated in sequence in FIGS. 2b-2d. Thus, the tapered mandrel remains within and supports the flared end throughout the extrusion process. Further, the extruded tube is preferably stretched between the extrusion nozzle and the tapered mandrel. If a relatively soft material is used, the extruded material may be arranged to be expelled in a downward or vertical direction, in order to avoid sagging and the like. Alternatively, holding means, such as a holding plate or the like, may be arranged to follow the extruded material during extrusion, and to maintain the extruded material in an essentially straight, and preferably essentially horizontal, position. The holding means is preferably arranged to be moved together with the mandrel during extrusion.

In step 207, the extruded tube is cut at a desired predetermined length, such that the tube can be removed for subsequent processing.

The thus formed open ended tube is useable for many applications, and for many types of medical tubular objects, and may e.g. be used as a urinary catheter. However, in case of e.g. urinary catheters, it is often preferred to have a rounded, closed tip portion, and drainage openings formed on the side of the catheter end. The tubular object producible in the above-discussed way may also be formed with such a closed distal end. For instance, an insertable end of the tubular object (i.e. the end opposite the flared end) can be formed into a rounded tip portion, in step 208, by e.g. melting and/or by forming at room temperature before drying. Further, one or more drainage openings can be formed in the tube wall, in step 209, by e.g. punching and/or blank cutting. The punching step might be prior to step 208 i.e prior to the forming and/or closing of the tip end. In order to accomplish punching, laser cut etc a pin might be inserted into the tube prior to punching, laser cutting etc, Hereby, drainage holes can easily be formed before closing of the tube end by forming a tip.

Figure 7:
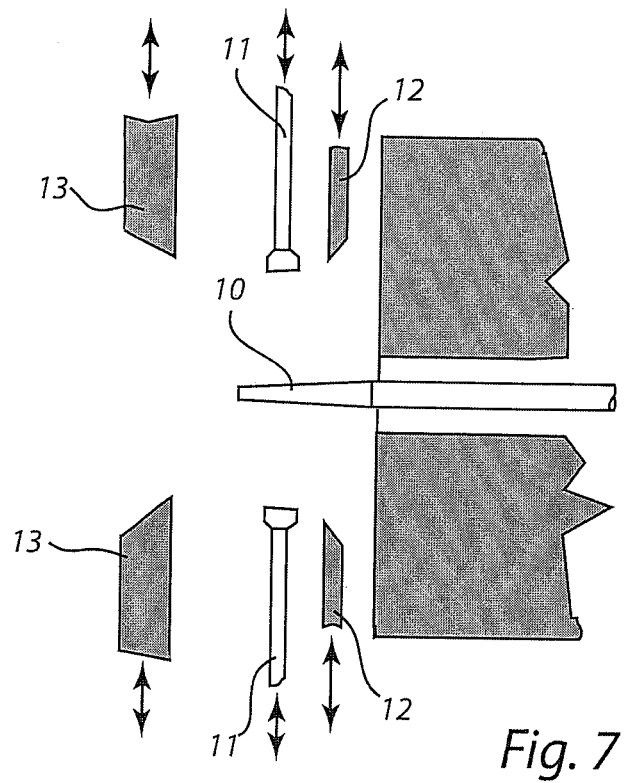
FIG. 7 schematically illustrate a tip forming apparatus which may be used in conjunction with the apparatus of FIG. 1.

FIG. 7 schematically illustrate a tip forming device which may be used in conjunction with the apparatus discussed above with reference to FIG. 1, and which may also form an integrated part of this apparatus. Here, the nozzle 3 of the extruder 2 is provided with a centrally protruding pin 10. The pin 10 preferably protrudes a certain distance, such as 1-3 cm, out from the extruder nozzle 3. Punching means 11 are arranged radially separated from the pin 10, and being moveable towards the pin 10 for punching holes in the tube. Alternatively, the punching means may use laser or the like for forming the holes, whereby no movement relative to the pin 10 is necessary.

Further, there is provided cutting means 12 radially separated from the pin, such as a mechanical cutting tool, a laser cutting tool or the like, for cutting of the extruded tube. In case a mechanical cutting tool is used, the cutting tool is preferably moveable towards the pin 10. The cutting tool is preferably moveable in a circle around the pin 10, to effect complete cutting of the tube. Alternatively, a plurality of cutting tools may be provided, which together effect the complete cutting along the circumference of the extruded tube.

The cutting tools are preferably arranged between the punching means 11 and the extruder 2. Hereby, the cutting may be effected either before, during of after the formation of the holes by the punching means 11.

Further, there is preferably provided tip forming means 13 for forming a rounded, closed tip. The tip forming means 13 preferably comprises two or more parts being moveable towards each other, and with inner surfaces being shaped to correspond to the desired shape of the closed tip portion. Thereby, clamping of the parts together around the tube end forms the tip portion to its desired shape. The moveable parts may be used without any additional heat. However, preferably, the moveable parts are heated at their forward ends, at the surfaces arranged to be in contact with the tube end, thereby effecting a certain degree of melting of the tube material.

The tip forming means 13 is preferably arranged at a certain distance from the pin 10 in the axial direction. Hereby, cutting and hole formation may be effected when the tube is still arranged on the pin 10, and thereafter the tube may be pulled, by the mandrel 4 and clamping arrangement 5, away from the pin 10, and to a position where the tip forming means 13 may form the tip portion.

When using the tip forming device shown in FIG. 7, the mandrel 4 will initially be brought to a position adjacent to, or abutting, the forward end of the centrally protruding pin 10. Since the centrally protruding pin has a relatively limited extension, adequate formation of the extruded tube over the mandrel 4 will still be feasible.

Figure 8:
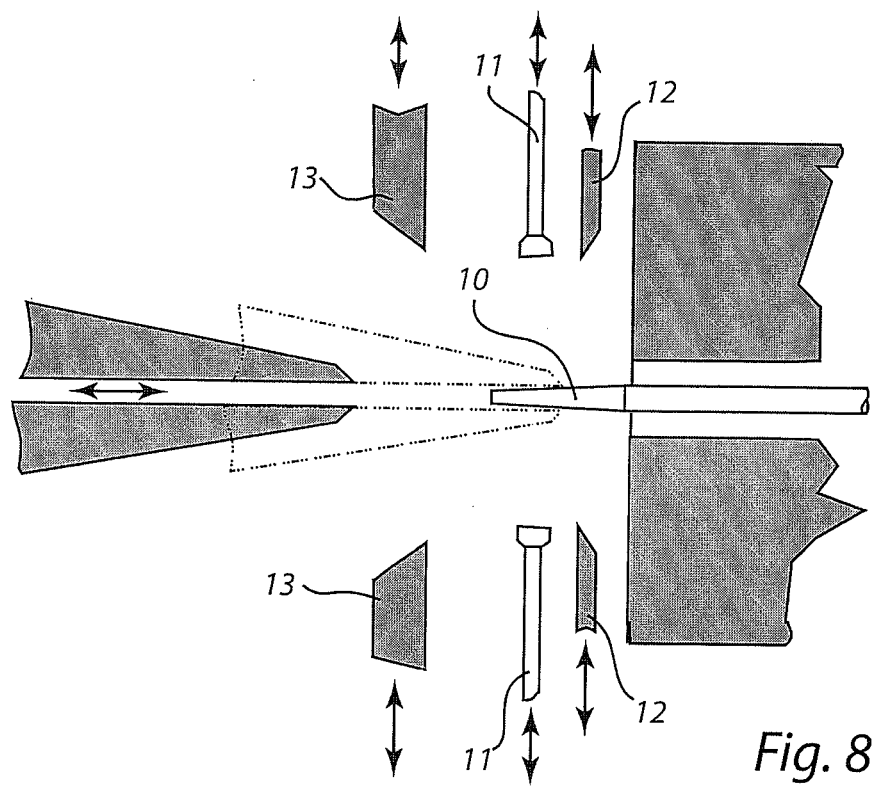
FIG. 8 schematically illustrate an alternative tip forming apparatus which may be used in conjunction with the apparatus of FIG. 1.

However, it is also possible to bring the mandrel closer to the extrusion opening. For example, this may be effected by providing an opening bore in the mandrel 4, and allowing the mandrel to be at least partly pushed over the centrally protruding pin 10, as is shown schematically in FIG. 8. Hereby, the mandrel may be arranged as close to the extruder opening as in the initially discussed embodiments, and still allowing a pin to extend out from the extruder nozzle for subsequent use in tip formation.

Figure 4:
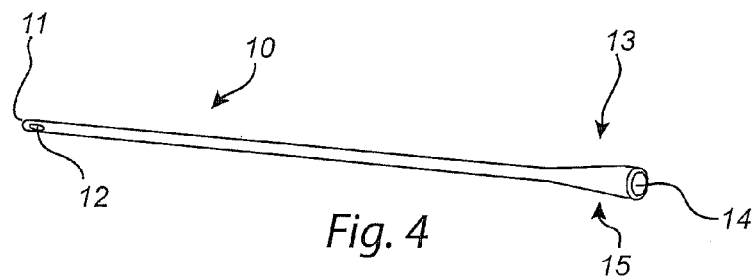
FIG. 4 schematically illustrates an embodiment of urinary catheter manufactured by the apparatus in FIG. 1.
Figure 5:
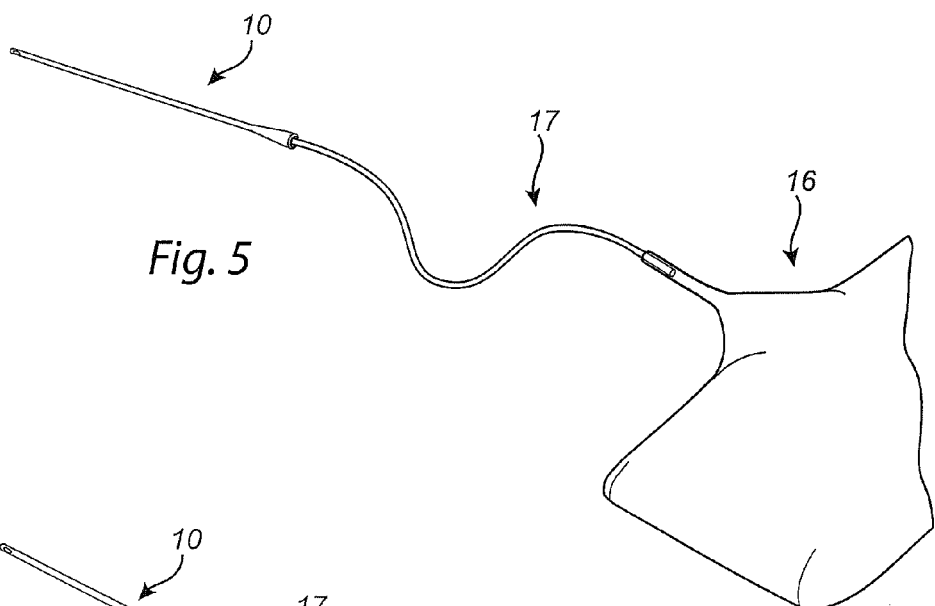
FIGS. 5 and 6 schematically illustrate how the flared end of the tube in FIG. 3 can be used to connect the tube to a receptacle.
Figure 6:
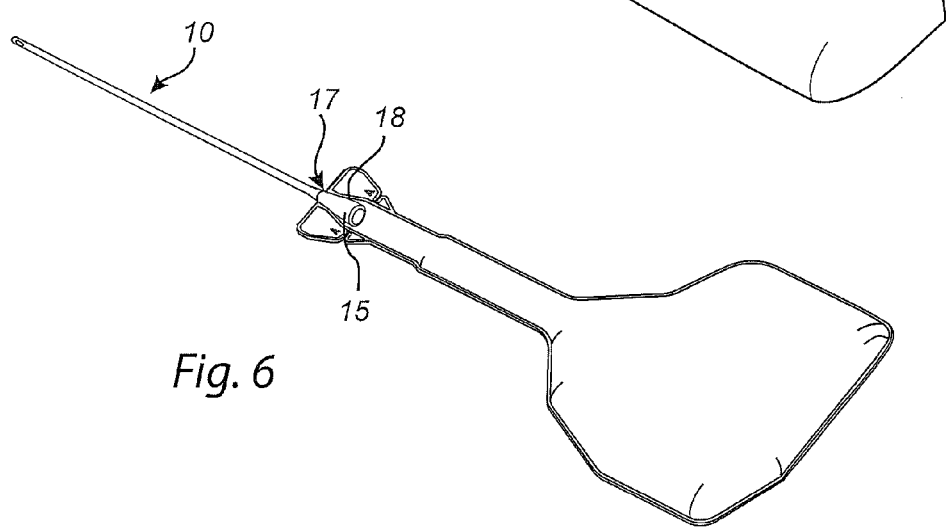

FIG. 4 schematically illustrates an example of a urinary catheter 10 manufactured according to the above described manufacturing process. The illustrated urinary catheter comprises an insertable end 11 provided with draining openings 12 to allow fluid to enter the tube, and a non-insertable end 13 provided with an outlet 14, being in fluid connection with the draining openings 12 via a lumen (not shown) of the tube. Further, the non-insertable end 13 of the tube is flared. The flared end may serve as a connector 15 for connecting the tube to a receptacle for collection of fluid. The flared connector 15 may be connected to the receptacle 16 by means of a tube 17 as illustrated in FIG. 5. An alternative is to arrange the catheter inside the receptacle 16, such that the catheter tube may be maneuvered through an opening 17 of the receptacle and pulled out until the flared end 15 forms a mechanical seal connection with the opening 17 at a restriction 18 of the receptacle, as illustrated in FIG. 6.

The catheters may be made in various lengths and dimensions. Typically, the length of the catheter tube for female catheters are in the range 50-200 mm, such as with a length in the size of 150 mm, and for male catheters may preferably in a length in the range of 180-450 mm, such as in the size of 400 mm. The indicated lengths refer to the length of the catheter tube excluding the flared end. Depending on the material, the tube may be subject to some degree of shrinkage during drying and cooling. In the exemplary degradable material discussed above, drying at 40° C. for 20 h typically decreases the diameter with 15-18%, and the length with 8-9%. The outer diameter of the tube after drying/cooling is preferably in the range 3-15 mm, and more preferably in the range 5-10 mm, and most preferably in the range 6-7 mm, such as 6.5 mm. The inner diameter of the tube after drying/cooling is preferably in the range 1-10 mm, and more preferably in the range 2-6 mm, and most preferably in the range 3-4 mm, such as 3.4 mm. The thickness of the tube after drying/cooling is preferably in the range 0.5-4 mm, and more preferably in the range 1-3 mm, and most preferably in the range 1.5-2 mm. The flared end preferably has an inner diameter at its largest end in the range 5-15 mm, and more preferably in the range 7-12 mm, and most preferably in the range 9-11 mm, such as 10.4 mm. The length of the flared end is preferably in the range 10-100 mm, and more preferably in the range 20-60 mm, and most preferably in the range 25-50 mm, such as 35 mm.

Specific embodiments of the invention have now been described. However, several alternatives are possible, as would be apparent for someone skilled in the art. For example, other types of extruders may also be used. Such and other obvious modifications must be considered to be within the scope of the present invention, as it is defined by the appended claims.

The invention claimed is:

1. An apparatus for manufacturing a medical tubular object as an extruded tube for insertion into a body passageway, comprising:
   an extrusion nozzle adapted to extrude a tube;
   an extruder arranged to push tube material through the extrusion nozzle in an extrusion direction;
   a cutting tool for cutting the extruded tube at a first predetermined length in a vicinity of the extrusion nozzle; and
   a tapered mandrel adjacent and in alignment with the extrusion nozzle and tapering toward the extrusion nozzle such that an initial part of the extruded tube is advanced onto the tapered mandrel as the extruded tube is being extruded, whereby a flared end is formed on the initial part of the extruded tube,
   wherein the tapered mandrel is moveable away from the extrusion nozzle such that moving the tapered mandrel away from the extrusion nozzle after a second predetermined length of the extruded tube has been advanced onto the mandrel prevents the rest of the extruded tube from being expanded by the tapered mandrel.

2. The apparatus of claim 1, wherein the medical tubular object is a catheter.

3. The apparatus according to claim 1, wherein the tapered mandrel is moveable along the extrusion direction.

4. The apparatus according to claim 1, wherein the tapered mandrel is moveable at a speed that substantially corresponds to a speed at which the extruded tube is produced.

5. The apparatus according to claim 1, wherein the tapered mandrel has a conical shape or a frusto-conical shape.

6. The apparatus according to claim 1, further comprising at least one clamp for securing the initial part of the extruded tube to the tapered mandrel.

7. The apparatus according to claim 1, further comprising at least one punch arranged in the vicinity of the extrusion nozzle for punching holes in the extruded tube.

8. The apparatus according to claim 1, wherein the extrusion nozzle further comprises a centrally protruding pin, wherein the extrusion nozzle is arranged to extrude the tube over the centrally protruding pin.

9. The apparatus according to claim 8, wherein the centrally protruding pin aligns and inserts into an opening bore at a tapered end of the tapered mandrel.

10. The apparatus according to claim 1, further comprising at least two moveable parts having inner surfaces shaped complementary to a predetermined shape for a closed tip portion of the extruded tube when the moveable parts are brought together around the closed tip portion of the extruded tube.

11. The apparatus according to claim 3, further comprising a guide rail, wherein the tapered mandrel is mounted and moveable on the guide rail to move along the extrusion direction.

12. The apparatus according to claim 1, further comprising a holding plate arranged below the tapered mandrel and the extrusion nozzle to support the extruded tube.

* * * * *